United States Patent [19]

Karrer

[11] 4,061,683
[45] Dec. 6, 1977

[54] DIPHENYL ETHER DERIVATIVES

[75] Inventor: Friedrich Karrer, Basel, Switzerland

[73] Assignee: Ciba-Geigy Corporation, Ardsley, N.Y.

[21] Appl. No.: 611,731

[22] Filed: Sept. 9, 1975

Related U.S. Application Data

[63] Continuation-in-part of Ser. No. 328,218, Jan. 31, 1973, abandoned.

[51] Int. Cl.² .............................................. C07C 43/22
[52] U.S. Cl. .......................... 260/613 R; 260/612 R; 260/348.49; 260/348.57; 424/340; 424/341; 424/278
[58] Field of Search ...................... 260/612 R, 613 R

[56] References Cited

U.S. PATENT DOCUMENTS

| | | | |
|---|---|---|---|
| 3,155,733 | 11/1964 | Reifschneider | 260/612 R |
| 3,170,959 | 2/1965 | Trapp | 260/613 R |
| 3,240,703 | 3/1966 | Symon et al. | 252/45.7 |
| 3,441,615 | 4/1969 | Merica | 260/613 R |
| 3,907,783 | 9/1975 | Pallos | 260/612 R X |

FOREIGN PATENT DOCUMENTS

| | | |
|---|---|---|
| 2,021,228 | 11/1970 | Germany. |
| 2,304,962 | 8/1973 | Germany. |

*Primary Examiner*—Bernard Helfin
*Attorney, Agent, or Firm*—Harry Falber

[57] ABSTRACT

Compounds of the formula

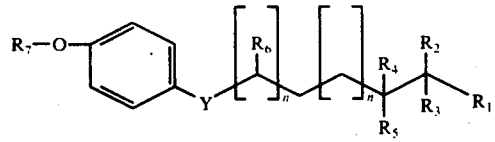

(I)

wherein
$R_1$ represents hydrogen, halogen, $C_1$–$C_4$-alkyl, vinyl or ethynyl,
$R_2$ represents hydrogen, halogen, methyl or ethyl, or $R_1$ and $R_2$ together represent the cyclopentyl or cyclohexyl ring,
$R_3$ represents hydrogen, halogen, methyl, ethyl or $C_1$–$C_4$-alkoxy,
$R_4$ represents hydrogen, halogen or methyl,
$R_5$ represents hydrogen or halogen, or
$R_3$ and $R_5$ together represent a carbon-carbon-bond, or an oxygen bridge,
$R_6$ represents hydrogen, methyl or ethyl,
$R_7$ represents cyclohexyl or the group

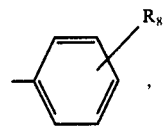

$R_8$ represents hydrogen, halogen, $C_1$–$C_4$-alkyl or $C_1$–$C_4$-alkoxy,
Y represents oxygen or the group

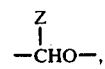

whereby the

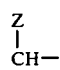

group is bound to the phenyl ring,
Z represents hydrogen or methyl, and
m and n each represent the number 0 or 1 a method for their manufacture and their use for the control of insects and members of the order acarina are disclosed.

9 Claims, No Drawings

DIPHENYL ETHER DERIVATIVES

This application is a continuation-in-part of co-pending application Ser. No. 328,218 filed on Jan. 31, 1973, now abandoned.

The invention relates to derivatives of 4-alkoxydiphenyl ethers or 4-alkozymethyldiphenyl ethers, or of 1-cyclohexyloxy-4-alkoxybenzenes or 1-cyclohexyloxy-4-alkoxymethylbenzenes, unsubstituted or substituted in the phenyl rings, to their production, and to their use for the control of the development of insects and members of the order acarina.

The compounds correspond to the formula

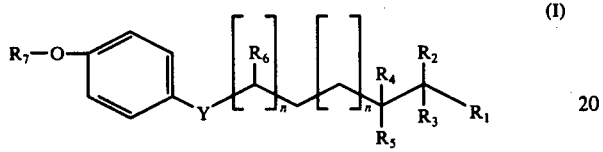

wherein
$R_1$ represents hydrogen, halogen, $C_1$-$C_4$-alkyl, vinyl or ethynyl,
$R_2$ represents hydrogen, halogen, methyl or ethyl, or
$R_1$ and $R_2$ together represent the cyclopentyl or cyclohexyl ring,
$R_3$ represents hydrogen, halogen, methyl, ethyl or $C_1$-$C_4$-alkoxy,
$R_4$ represents hydrogen, halogen or methyl,
$R_5$ represents hydrogen or halogen, or
$R_3$ and $R_5$ together represent a carbon-carbon-bond, or an oxygen bridge,
$R_6$ represents hydrogen, methyl or ethyl,
$R_7$ represents cyclohexyl or the group

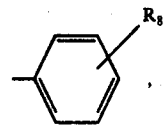

$R_8$ represents hydrogen, halogen, $C_1$-$C_4$-alkyl or $C_1$-$C_4$-alkoxy,
Y represents oxygen or the group

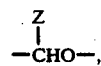

whereby the

group is bound to the phenyl ring,
Z represents hydrogen or methyl, and
m and n each represent the number 0 or 1.

By halogen are meant fluorine, chlorine, bromine or iodine, particularly, however, chlorine.

The alkyl and alkoxy groups in the case of $R_1$, $R_3$ and $R_7$ can be straight-chain or branched. Examples of such groups include methyl, ethyl, n-propyl, isopropyl, i-, n-, sec.-, tert.-butyl, methoxy and ethoxy.

Compounds forming a preferred group are compounds of formula I wherein $R_1$ represents hydrogen, chlorine, methyl, ethyl, n-propyl, isopropyl, n-, i-, sec.-butyl, vinyl or ethynyl,
$R_2$ represents hydrogen, chlorine or methyl, or
$R_1$ and $R_2$ together represent the cyclopentyl or cyclohexyl ring,
$R_3$ represents hydrogen, methyl, ethyl, methoxy or ethoxy,
$R_4$ represents hydrogen, chlorine or methyl,
$R_5$ represents hydrogen, or
$R_3$ and $R_5$ together represent a carbon-carbon-bond or an oxygen bridge,
$R_6$ represents hydrogen or methyl,
$R_7$ represents cyclohexyl or the group

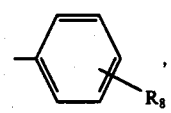

$R_8$ represents hydrogen, chlorine, methyl, ethyl or ethoxy,
Y represents oxygen, or the group

whereby the

group is bound to the phenyl ring,
Z represents hydrogen or methyl, and
m and n each represent the number 0 or 1.

Compounds to be particularly emphasised because of their effectiveness are compounds of formula I wherein
$R_1$ represents hydrogen, chlorine, methyl, ethyl, n-propyl, isopropyl, n-, i-, sec.-butyl, vinyl or ethynyl,
$R_2$ represents hydrogen, chlorine or methyl,
$R_3$ represents hydrogen, methyl, ethyl, methoxy or ethoxy,
$R_4$ represents hydrogen, chlorine or methyl,
$R_5$ represents hydrogen, or
$R_3$ and $R_5$ together represent a carbon-carbon-bond, or an oxygen bridge,
$R_6$ represents hydrogen or methyl,
$R_7$ represents the group

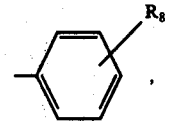

$R_8$ represents hydrogen, chlorine, methyl, ethyl or ethoxy,
Y represents oxygen, or the group —$CH_2O$—, whereby the $CH_2$— group is bound to the phenyl ring, and
m and n each represent the number 0 or 1.

The compounds of formula I are produced in a manner known per se by the following methods:

1. Formation of the ether (O-alkylation) by condensation of a halide of formula III with a compound of formula II:

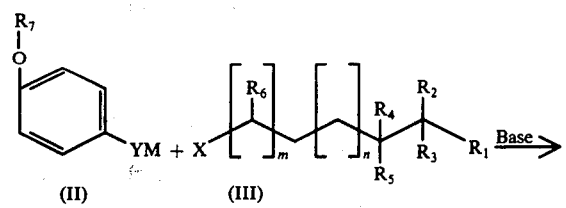

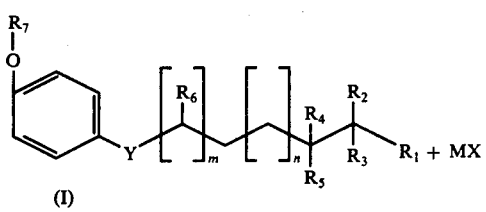

whereby also in formulae II and III, $R_1$ to $R_7$, Y, m and n have the meanings given for formula I; X stands for chlorine, bromine or iodine, preferably for chlorine or bromine; M is a metal, especially the I. or II. main group of the periodic system, or hydrogen 2. Epoxidation of a compound of formula IB:

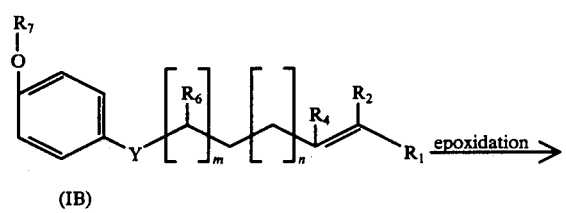

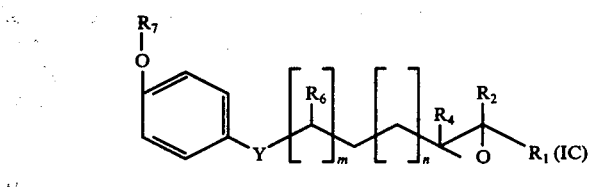

whereby in formulae IB and IC: $R_1$, $R_2$, $R_4$, $R_6$, $R_7$, Y, m and n have the meanings given for formula I.

3. Addition of hydrogen halide to the olefinic double bond of a compound of formula IB:

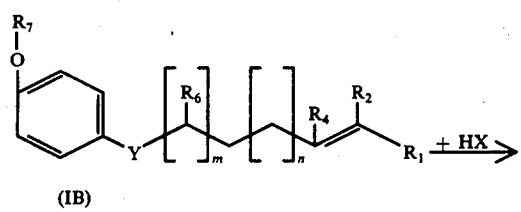

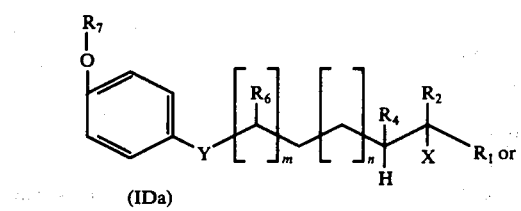

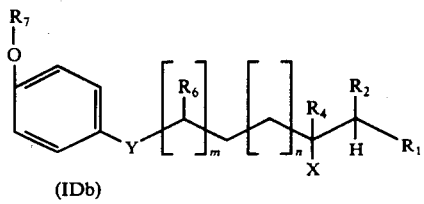

whereby in formulae IB, IDa and IDb, $R_1$, $R_2$, $R_4$, $R_6$, $R_7$, Y, m and n have the meanings given for formula I; X stands for halogen, preferably, however, for chlorine.

4. Epoxidation of an unsaturated halide to give an epoxy halide, and condensation thereof with a compound of formula II:

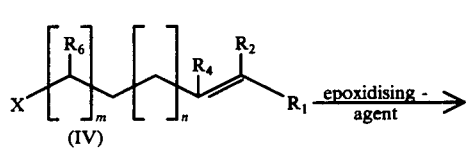

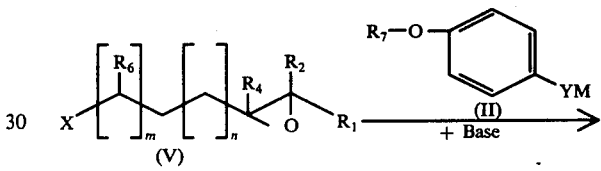

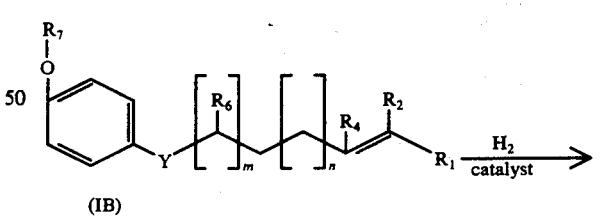

whereby in formulae IC, II, IV and V, $R_1$, $R_2$, $R_4$, $R_6$, $R_7$, Y, m, n and M have the meanings given in the case of formula I or given above; X stands for halogen, especially for bromine or chlorine.

5. Hydrogenation of a compound IB:

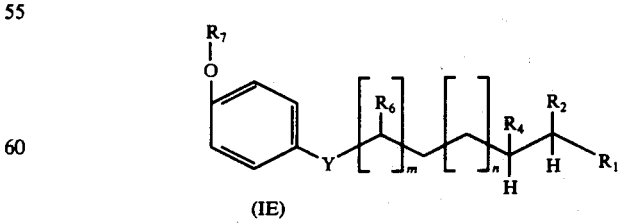

whereby $R_1$, $R_2$, $R_4$, $R_6$, $R_7$, Y, m and n have the meanings given for formula I.

6. Selective hydrogenation of a conjugated triple bond to a conjugated double bond:

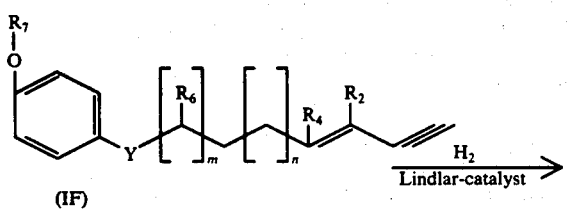

(IF)

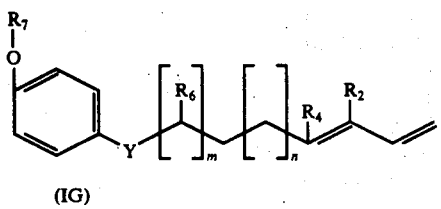

(IG)

whereby $R_2$, $R_4$, $R_6$, $R_7$, Y, m and n have the meanings given for formula I.

7. Addition of an alcohol or water to a double bond:

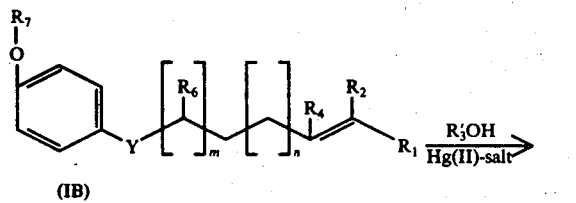

(IB)

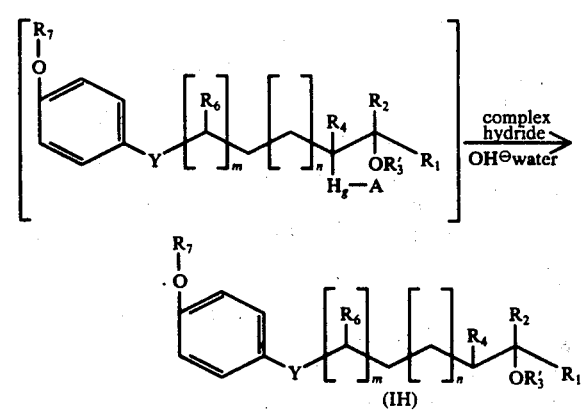

(IH)

whereby $R_1$, $R_2$, $R_4$, $R_6$, $R_7$, Y, m and n have the meanings given for formula I, A represents the anion of an Hg(II)-salt and $R'_3$ represents a $C_1$-$C_4$-alkyl radical or hydrogen.

The mercury (II)-salt used is preferably mercury acetate or mercury fluoroacetate.

8. Alkylation of an alcohol of formula IJ:

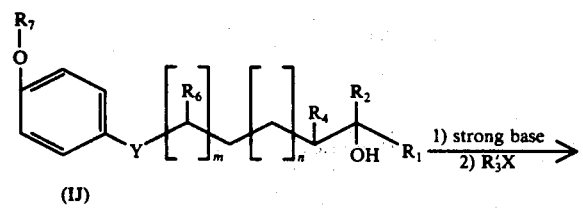

(IJ)

-continued

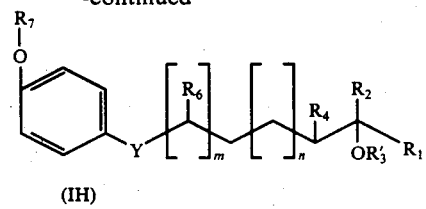

(IH)

whereby $R_1$, $R_2$, $R_4$, $R_6$, $R_7$, Y, m and n have the meanings given for formula I, X represents a halogen atom, and $R'_3$ represents a $C_1$-$C_4$-alkyl radical.

The alkylation of 4-hydroxydiphenyl ether and of 4-cyclohexyloxy-phenol, respectively, or of their derivatives substituted in the rings, can be performed with the various saturated or unsaturated halides, depending on the reactivity of the applied halide, in various solvents and at various reaction temperatures, always, however, in the presence of at least one mole of a base.

Suitable solvents are, in particular, acetone, methyl ethyl ketone, cyclohexanone, 1,2-dimethoxyethane, tetrahydrofuran, dioxane, dialkyl ether, dimethylformamide, dimethylsulphoxide, hexamethylphosphoric acid triamide, sulpholane, inert hydrocarbons such as toluene, benzene, xylene and suchlike. It is possible, however, to use other solvents.

The necessary bases and acid acceptors, respectively, used in the case of ether formation from a compound of formula II and a halide, are, in particular, alkali or alkaline-earth hydroxides, alkali or alkaline-earth carbonates, alkali or alkaline-earth hydrides and alkali alkoxides; it is possible, however, also to use organic bases such as, e.g. triethylamine, pyridine, and so forth, as acid acceptors.

The reaction temperatures for the formation of arylalkyl ethers are between $-10°$ and $130°$ C, mostly between 5° and 70° C (e.g. with application of solvents such as dimethylsulphoxide, dimethylformamide, dioxane, sulpholane, tetrahydrofuran, hexamethylphosphoric acid triamide, 1,2-dimethoxyethane, etc.); or the reaction is performed at the boiling temperature of the employed solvent (e.g. in the case of ketones).

The conversion of compounds of formula IB into the corresponding epoxy derivatives is performed preferably in an inert solvent, advantageously in a chlorinated hydrocarbon between $-25°$ C and room temperature, usually between $-5°$ and $+5°$ C, with the aid of an epoxidising agent, such as, e.g. a peroxy acid. The epoxy derivatives of formula IC can also be obtained by way of the corresponding halohydrines, by the cleavage of hydrogen halide, the process comprising the conversion of an alkenyl ether of formula IB with an N-halosuccinimide, e.g. with N-bromosuccinimide, in a mixture of water and a solvent such as tetrahydrofuran, 1,2-dimethoxyethane, dioxane or tert.butanol in the homogeneous or heterogeneous phase between $-5°$ C and room temperature, into bromohydrine; and the obtainment, by the subsequent treatment of the bromohydrin with an alkaline agent such as, e.g. alkali carbonate or an alkali alkoxide, of the desired epoxy derivative. By alkali is meant, in particular, sodium or potassium.

The term "peroxy acid" signifies principally lower peroxyalkanoic acids having 1 to 6 carbon atoms, such as, e.g. peroxyacetic acid, as well as aromatic peroxyacids such as peroxybenzoic acid, monoperoxyphthalic acid, particularly, however, 3-chloroperoxybenzoic acid.

The processing and isolation of compounds of formula I are effected by known techniques; e.g., addition of water or ice to the reaction mixture; subsequent extraction with a suitable solvent, e.g. ether; washing of the organic phase, e.g. with dilute alkali solution or alkali carbonate; and drying of the solution over anhydrous sodium sulphate. After removal of the solvent, the obtained compound of formula I can, if necessary, be purified by crystallisation, vacuum distillation, or chromatography on silica gel or aluminium oxide.

Various reaction sequences can be employed to obtain epoxidised compounds of formula IC: They are obtained either by a process in which, as according to the stated production processes, the hydroxyl group of 4-hydroxydiphenyl-ether- or 4-cyclohexyloxyphenol-compounds is firstly etherified, in the presence of a base, with an alkenyl halide, and in this arylalkenyl-ether the olefinic double bond subsequently converted, as described above, into an epoxy; or the alkenyl halide firstly epoxidised, with the exclusion of moisture, in a chlorinated hydrocarbon, between $-25°$ C and room temperature, with the aid of an epoxidising agent, such as, e.g. a peroxy acid, and this epoxy halide reacted in the consequent reaction with 4-hydroxydiphenyl ether and 4-cyclohexyloxy-phenol, in the presence of an acid acceptor, to the final products, an epoxidised diphenyloxide-alkyl ether and 4-cyclohexyloxyphenyl-alkyl ether, respectively.

The addition of hydrogen halide, especially of hydrogen chloride or bromide, to an aliphatic double bond is effected preferably by the action of the anhydrous hydrogen halide on a 4-alkenyloxydiphenyl ether or on a 4-alkenyloxy-1-cyclohexyloxybenzene derivative in a suitable solvent, such as, e.g. a chlorinated hydrocarbon, methanol, ethanol, another alcohol, a dialkyl ether, glacial acetic acid, etc. The addition of the hydrogen halide is performed at a temperature of between $-30°$ and $+25°$ C.

The isolation of the yellowish halide is carried out likewise by known techniques, such as addition of water to the reaction mixture, extraction with an organic solvent, and removal of the excess hydrogen halide by neutralisation with a weak base, or by washing with water, whereby, after removal of the solvent, the halide remaining can be further purified by crystallization, high vacuum distillation, or chromatography.

Unsaturated araliphatic ethers of formula IB can be hydrogenated in a known manner to the saturated araliphatic ethers of formula IE, e.g. with catalytically activated hydrogen, advantageously between room and boiling temperature of the reaction mixture under normal or elevated pressure. Suitable catalysts are preferably Raney nickel, or noble metals such as platinum or palladium. Applicable solvents are, in particular, methyl and ethyl acetate, dioxane, or alcohols such as methanol, ethanol, and so forth.

Unsaturated araliphatic ethers of formula IF can be selectively partially hydrogenated, in a known manner, to ethers of formula IG, e.g. with catalytically activated hydrogen, at room temperature and normal pressure, until one mole of hydrogen is absorbed. The catalyst preferably employed is a Lindlar catalyst. Suitable solvents are, e.g. acetic acid methyl and -ethyl ester, dimethoxy ethane, dioxane, or alcohols such as methanol or ethanol.

The reactions to the active substance of formula I wherein $R_3$ represents a $C_1$-$C_4$-alkoxy group are performed under normal pressure and in an anhydrous alcohol $R'_3OH$, and, if necessary, in solvents and diluents inert to the reactants, e.g. in ethers such as tetrahydrofuran, dioxane, diethyl ether, 1,2-dimethyloxyethane, etc. In the (1) step — if $R'_3 = H$ — as well as in the (2) step, the solvent can also be water.

The mercury-(II)-salts preferably used are mercury-(II)-acetate and mercury-(II)-trifluoroacetate. The complex hydride employed is, e.g. $MeBH_4$, wherein Me represents an alkali metal atom or alkaline-earth metal atom. The reaction with complex hydride is performed in the presence of alkali hydroxide and water. The reaction temperatures are in the range of $-10°$ to $+40°$ C, preferably between $0°$ and $+25°$ C.

A further method of obtaining compounds of formula I wherein $R_3$ represents a $C_1$-$C_4$-alkoxy group comprises moreover the etherification of an alcohol of formula IJ by reaction with a halide, depending on the reactivity of the applied halide, in various solvents and at different reaction temperatures, always, however, in the presence of at least one mole of one of the above mentioned bases.

The obtained compounds occur, where this is, in principle, possible, as cis/trans-isomer mixtures. An isomer mixture can be separated, e.g. with the aid of chromatographic separation methods into the isomeric forms; for example, by adsorption on a separating material having selective adsorption activity, such as, e.g silica gel, aluminium oxide, and subsequent elution of the separated isomers with a suitable solvent such as, e.g. diethyl ether, hexane, methyl or ethyl acetate. A further chromatographic separation method is gas chromatography. In certain cases, an isomer mixture can be separated also by fractional distillation or by fractional crystallisation.

The starting materials of formulae II to V are known compounds, which can be produced analogously to known methods described in the literature.

The compounds of formula I are suitable for the control of the most diverse animal pests.

They are suitable for the control of insects, and members of the order acarina, principally, however, for the control of insects. Especially good results are obtained against insects of the order Diptera such as Culicidae and Muscidae and the order Coleoptera such as Dermestidae and Tenebrionidae.

Moreover, the compounds of formula I can be used against, for example, insects of the following orders and families:

| | |
|---|---|
| Orthoptera | Acrididae |
| | Gryllidae |
| | Blattidae |
| Isoptera | Kalotermitidae |
| Hemiptera | Miridae |
| | Piesmidae |
| | Lygaeidae |
| | Pyrrhocoridae |
| | Pentatomidae |
| | Cimicidae |
| | Reduviidae |
| | Jassidae |
| | Eriosomatidae |
| | Lecaniidae |
| Coleoptera | Carabidae |
| | Elateridae |
| | Coccinellidae |
| | Tenebrionidae |
| | Dermestidae |
| | Cucujidae |
| | Chrysomelidae |

| | |
|---|---|
| Lepidoptera | Curculionidae |
| | Scolytidae |
| | Scarabaeidae |
| | Pyralidae |
| | Phyticidae |
| | Pyraustidae |
| | Crambidae |
| | Tortricidae |
| | Gralleriidae |
| | Lyonetiidae — Noctuidae |
| | Yponomeutidae — Pieridae |
| | Plutellidae — Lymantriidae |
| Diptera | Culicidae |
| | Simuliidae |
| | Tipulidae |
| | Muscidae |

The action of the compounds of formula I can be appreciably broadened and enhanced, and adapted to suit given circumstances, by the addition of other insecticides and/or acaricides or insect bait.

Suitable additives include, for example, the following active substances:
Organic phosphorus compounds
Nitrophenols ans derivatives
Pyrethroides
Formamidines
Urea derivatives
Carbamates
Chlorinated Hydrocarbons The compounds of formula I can be used on their own or together with suitable carriers and/or additives. Suitable carriers and additives can be solid or liquid and correspond to the substances common in formulation practice, such as, e.g. natural or regenerated substances, solvents, dispersing agents, wetting agents, adhesives, thickeners, bonding agents and/or fertilisers. For application, the compounds of formula I can be processed into the form of dusts, emulsion concentrates, granulates, dispersions, sprays or solutions, the formulation of the said preparations being effected in a manner commonly known in practice.

The agents according to the invention are produced in a manner known per se by the intimate mixing and/or grinding of active substances of formula I with suitable carriers, optionally with the addition of dispersing agents or solvents which are inert to the active substances. The active substances can be obtained and used in the following preparation forms:

Solid forms:
Dusts, scattering agents, granules, coated granules, impregnated granules and homogeneous granules.
Liquid forms:
a. active substances which are dispersible in water: wettable powders, pasts, emulsions;
b. solutions.

To manufacture solid forms (ducts, scattering agents), the active substances are mixed with solid carriers. Suitable carriers are, for example: kaoline, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

Granules can be very easily manufactured by dissolving an active substance of the formula I in an organic solvent and applying the resulting solution to a granulated material, for example attapulgite, $SIO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilise the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilise the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salts of oleoyl methyl tauride, ditertiary acetylene glycols, dialkyl dilauryl ammonium chlorine and fatty acid alkali and alkaline earth metal salts.

Suitable anti-foam agents are silicones.

The active substances are mixed, ground, sieved and strained with the additives cited hereinabove in such a manner that, the size of the solid particles does not exceed 0.02 to 0.04 μ in wettable powders, and 0.03 μ in pastes. To produce emulsifiable concentrates and pastes, dispersing agents such as those cited above, organic solvents, and water are used. Examples of suitable solvents are: alcohols, benzene, xylene, toluene, dimethyl sulphoxide, and mineral oil fractions which boil between 120° and 350° C. The solvents must be practically odourless, not phytotoxic, and inert to the active substances.

Furthermore, the agents according to the invention can be applied in the form of solutions. For this purpose the active substances, or several active substances of the general formula I, are dissolved in suitable organic solvents, mixtures of solvents or in water. Aliphatic and aromatic hydrocarbons, chlorinated derivatives thereof, alkyl naphthalenes, and mineral oils, singly or in admixture with each other, can be used as organic solvents.

The content of active substance in the above described agents is between 0.1 to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:
a. 5 parts of active substance
   95 parts of talcum
b. 2 parts of active substance
   1 part of highly disperse silicic acid
   97 parts of talcum.

The active substances are mixed with the carriers and ground.

Granules

The following substances are used to produce 5% granules:
   5 parts of active substance,
   0.25 parts of epichlorohydrin,
   0.25 parts of cetyl polyglycol ether,
   3.50 parts of polyethylene glycol,
   91 parts of kaolin (particle size 0.3–0.8 mm).

The active substance is mixed with epichlorohydrin and dissolved with 6 parts of acetone; the polyethylene glycol and cetyl polyglycol ether are then added. The thus obtained solution is sprayed on kaolin, and the acetone subsequently evaporated in vacuo.

Wettable Powder

The followng constituents are used for the preparation of (a) a 40%, (b) and (c) a 25%, and (d) a 10% wettable powder:
a. 40 parts of active substance,
   5 parts of sodium lignin sulphonate,
   1 part of sodium dibutyl-naphthalene sulphonate,
   54 parts of silicic acid.
b. 25 parts of active substance,
   4.5 parts of calcium lignin sulphonate,
   1.9 parts of Champagne chalk/hydroxyethyl cellulose mixture (1:1),
   1.5 parts of sodium dibutyl naphthalene sulphonate,
   19.5 parts of silicic acid,
   19.5 parts of Champagne chalk,
   28.1 parts of kaolin.
c. 25 parts of active substance,
   2.5 parts of isooctylphenoxy-polyoxyethylene-ethanol,
   1.7 parts of Champagne chalk/hydroxyethyl cellulose mixture (1:1),
   8.3 parts of sodium aluminium silicate,
   16.5 parts of kieselguhr,
   46 parts of kaolin.
d. 10 parts of active substance,
   3 parts of a mixture of the sodium salts of saturated fatty alcohol sulphates,
   5 parts of naphthalenesulphonic acid/formaldehyde condensate,
   82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable Concentrates

The following substances are used to produce (a) a 10% and (b) a 25% and (c) a 50% emulsifiable concentrate:
a. 10 parts of active substance,
   3.4 parts of epoxidised vegetable oil,
   3.4 parts of a combination emulsifier consisting of fatty alcohol polyglycol ether and alkylarylsulphonate calcium salt,
   40 parts of dimethylformamide,
   43.2 parts of xylene.
b. 25 parts of active substance,
   2.5 parts of epoxidised vegetable oil,
   10 parts of an alkylarylsulphonate/fatty alcohol-polyglycol ether mixture
   5 parts of dimethylformamide,
   57.5 parts of xylene.
c. 50 parts of active substance
   4,2 parts of tributyl phenol polyglycol ether
   5,8 parts of dodecylbenzolsulfonate calcium salt
   20 parts of cyclohexanone
   20 parts of xylene From these concentrates it is possible to produce, by dilution with water, emulsions of any desired concentration.

Spray

The following constituents are used to prepare (a) a 5% and (b) a 95% spray:
a. 5 parts of active substance,
   1 part of epichlorohydrin, 94 parts of benzine (boiling limits 160°–190° C).
b. 95 parts of active substance,
   5 parts of epichlorohydrin.

EXAMPLE 1

The solution of 6.4 g of ca. 90% potassium hydroxide in 90 ml of absolute ethanol was added dropwise at room temperature in the course of 6 hours, with stirring, to a solution of 19.2 g of 4-cyclohexyloxy-phenol and 16.4 g of 1-bromo-3-methyl-2-pentene in 150 ml of 1,2-dimethoxyethane. After the addition of the base, stirring was continued for a further 15 hours at room temperature. The precipitated potassium bromide was filtered off in subsequent processing, the filtrate concentrate in vacuo, the residue taken up in hexane, washed three times with ice cold 10% potassium hydroxide solution and then with water until neutral. After drying of the organic phase over sodium sulphate, filtration, and complete removal of the solvent in vacuo, there remained pure 1-cyclohexyloxy-4-(3-methyl-2-pentenyl-1-oxy)-benzene; $n_D^{20}$: 1.5265 (compound 1).

EXAMPLE 2

The solution of 10.3 g of 84% 3-chloroperoxybenzoic acid in 100 ml of methylene chloride diethyl ether (9:1) was added dropwise at −5° C in the course of ca. 5 hours to a solution of 13.7 g of 1-cyclohexyloxy-4-(3-methyl-2-pentenyl-1-oxy)-benzene in 150 ml of methylene chloride. The temperature was maintained at 0° C overnight; n-hexane was then added to the reaction mixture, and the whole washed three times with ice cold 10% potassium hydroxide solution and subsequently with water until neutral. After drying of the organic solution over sodium sulphate, filtration was performed, the solvent removed in vacuo, and the oily residue purified by chromatography on silica gel (eluting agent: ether/hexane 1:4) to thus obtain pure 1-cyclohexyloxy-4-(2,3-epoxy-3-methyl-pentyl-1-oxy)-benzene; $n_D^{20}$: 1.5180 (Cpd. 2).

EXAMPLE 3

The solution of 10.7 g of 1-(p-phenoxy)-phenoxy-3-methyl-2-pentene in 50 ml of absolute methanol was added in 10 minutes, with vigorous stirring, to a suspension cooled to −2° C of 12.7 g of pulverised mercury (II)-acetate in 80 ml of absolute methanol. Thirty minutes after addition of the alkene, additions were made, to the reaction mixture at −2° C, of 40 ml of a 3N aqueous sodium hydroxide solution and, immediately afterwards, of 40 ml of a 0.5 molar sodium hydride solution in 3N sodium hydroxide solution, the temperature consequently rising to ca. 25° C. Stirring was subsequently continued for 2 hours at 15°–20° C. In further processing, the reaction mixture was decanted from the precipitated mercury, the overlying solution poured on 500 ml of saturated sodium chloride solution, and the whole extracted four times with diethyl ether. The combined ether solutions were washed with sodium chloride solution, dried over sodium sulphate, and the solvent completely removed in vacuo. The oily residue was further purified by chromatography on silica gel (eluant: diethyl ether/hexane 1:5) to obtain pure 1-(p-phenoxy)-phenoxy-3-methyl-3-methoxypentane; $n_D^{20}$: 1.5440 (Cpd. 3).

EXAMPLE 4

An amount of 22 g of 1,3-dichloropropene was added dropwise at 55° C within 30 minutes, with stirring, to the mixture of 28 g of 4-hydroxydiphenyl ether, 150 ml of acetone, 26.6 g of anhydrous pulverised potassium carbonate and 50 ml of hexamethylphosphoric acid triamide, and the mixture held for a further 18 hours at the reflux temperature. The reaction mixture was subsequently poured on ca. 1.5 liters of ice water, and repeatedly extracted with diethyl ether. The combined ether solutions were washed four times with 10% potassium hydroxide solution and repeatedly, to obtain a neutral reaction, with saturated sodium chloride solution. After drying of the ether solution over sodium sulphate, the solvent was fully removed in vacuo to obtain pure 3-(p-phenoxy)-phenoxy-1-chloro-1-propene; $n_D^{20}$: 1.5819 (Cpd. 4).

EXAMPLE 5

13.2 g of 5-(p-phenoxy)-phenoxy-3-methyl-3-penten-1-ine (produced from 4-hydroxydiphenyl ether and 1-bromo-3-methyl-2-penten-1-ine in the presence of potassium carbonate in acetone; $n_D^{20}$: 1.5814) was taken up in 140 ml of 95% ethanol, and hydrogenated, at low-pressure and at room temperature, with 1.3 g of Lindlar catalyst, with addition of 0.5 g of quinoline, until hydrogen absorption ceased. In subsequent processing, the catalyst was filtered off, the ethanol distilled off from the filtrate, the residue taken up in ether/hexane (1:2), and this solution firstly repeatedly washed with ice-cold N-hydrochloric acid, and finally with water until neutral. After drying of the ether solution over sodium sulphate, the solvent was completely removed, and the oily 5-(p-phenoxy)-phenoxy-3-methyl-1,3-pentadiene further purified by chromatography on silica gel (eluant: ether/hexane 1:4); $n_D^{20}$: 1.5710 (Cpd. 5).

EXAMPLE 6

6.3 g of 90% pulverised potassium hydroxide was added in portions at ca. 10° C to the solution of 18.6 g of 4-hydroxydiphenyl ether in 125 ml of dimethylsulphoxide, and dissolved. To this solution there was then added dropwise within 3 hours at 10°–15° C, with stirring, 17.8 g of 1-bromo-4-methyl-3-hexene. After addition of the halide, stirring was continued for a further 20 hours at room temperature. In subsequent processing, the reaction mixture was poured into ca. 1 liter of ice water, and the mixture repeatedly extracted with diethyl ether. The combined ether phases were washed twice with water, four times with 20% aqueous potassium hydroxide solution, and finally again with water, until neutral. After drying of the ether phase over sodium sulphate, the solvent was distilled off, and the oil-like product remaining further purified by chromatography on silica gel (eluant: ether/hexane 1:5) to obtain pure 1-(p-phenoxy)-phenoxy-4-methyl-3-hexene; $n_D^{20}$: 1.5580 (Cpd. 6).

The following compounds are produced in a manner analogous to that described in Examples 1 to 6:

| Cpd. No. | Active substance | Physical data |
|---|---|---|
| 7 | C₆H₅—O—C₆H₄—O—CH₂—CH=C(CH₃)₂ | $n_D^{20}$: 1.5667 |
| 8 | C₆H₅—O—C₆H₄—O—CH₂—CH(—O—)C(CH₃)₂ (epoxide) | M.P.: 40–41° C |
| 9 | C₆H₅—O—C₆H₄—O—CH₂—CH=C(CH₃)—CH₂—CH₃ | $n_D^{20}$: 1.5589 |
| 10 | C₆H₅—O—C₆H₄—O—CH₂—CH(—O—)C(CH₃)(CH₂—CH₃) (epoxide) | M.P.: 50–52° C |
| 11 | C₆H₅—O—C₆H₄—O—CH₂—CH₂—C(CH₃)₃ | $n_D^{20}$: 1.5399 |
| 12 | C₆H₅—O—C₆H₄—O—CH₂—C(CH₃)=C(CH₃)(CH₃) | $n_D^{20}$: 1.5640 |
| 13 | C₆H₅—O—C₆H₄—O—CH₂—CH=C(Cl)(CH₃) | $n_D^{20}$: 1.5770 |
| 14 | C₆H₅—O—C₆H₄—O—CH(CH₃)—CH₂—CH₂—CH=C(CH₃)₂ | $n_D^{20}$: 1.5436 |
| 15 | C₆H₅—O—C₆H₄—O—CH(CH₃)—CH₂—CH₂—CH(—O—)C(CH₃)₂ (epoxide) | $n_D^{20}$: 1.5413 |
| 16 | C₆H₅—O—C₆H₄—O—CH₂—CH₂—CH(CH₃)₂ | $n_D^{20}$: 1.5453 |
| 17 | C₆H₅—O—C₆H₄—O—CH₂—CH₂—CH=C(CH₃)₂ | $n_D^{20}$: 1.5581 |
| 18 | C₆H₅—O—C₆H₄—O—CH₂—CH(—O—)C(CH₃)(C≡CH) (epoxide) | M.P.: 45–47° C |
| 19 | C₆H₅—O—C₆H₄—O—CH₂—CH=C(CH₃)—C≡CH | $n_D^{20}$: 1.5814 |

| Cpd. No. | Active substance | Physical data |
|---|---|---|
| 20 | 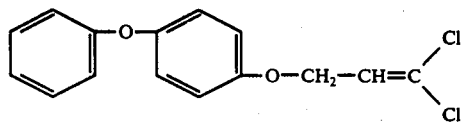 | M.P.: 31–32° C |
| 21 | 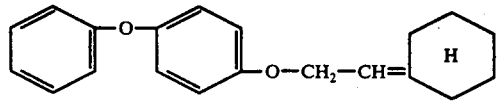 | M.P.: 55–57° C |
| 22 | 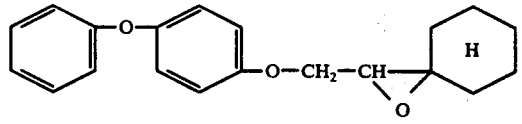 | M.P.: 82–84° C |
| 23 | 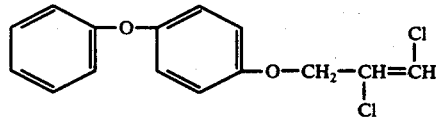 | $n_D^{20}$: 1,5887 |
| 24 | 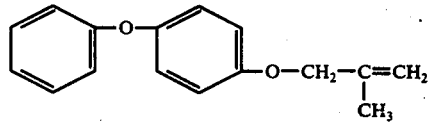 | M.P.: 30–32° C |
| 25 | 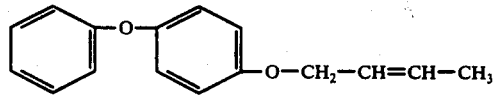 | M.P.: 39–41° C |
| 26 | 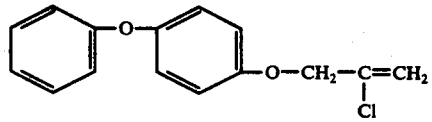 | $n_D^{20}$: 1,5789 |
| 27 | 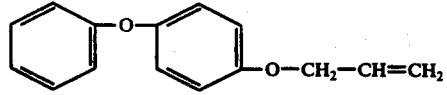 | $n_D^{20}$: 1,5739 |
| 28 | 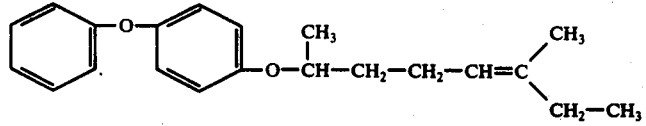 | $n_D^{20}$: 1,5364 |
| 29 | 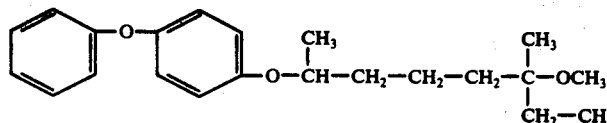 | $n_D^{20}$: 1,5350 |
| 30 | 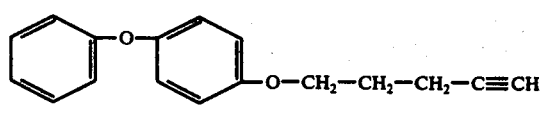 | $n_D^{20}$: 1,5652 |
| 31 | 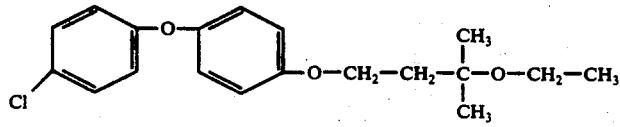 | $n_D^{20}$: 1,5444 |
| 32 | 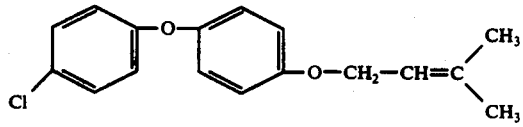 | M.P.: 67–68° C |
| 33 | 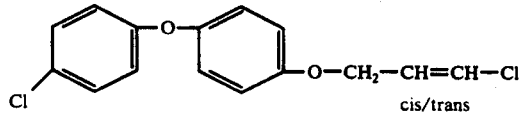 cis/trans | M.P.:35° C $n_D^{20}$: 1,5905 (undercooled melt) |

-continued

| Cpd. No. | Active substance | Physical data |
|---|---|---|
| 34 | C₆H₅–O–C₆H₄–O–CH₂–CH₂–CH(CH₃)–OCH₃ | $n_D^{20}$: 1.5458 |
| 35 | 4-C₂H₅–C₆H₄–O–C₆H₄–O–CH₂–CH=C(CH₃)–CH₂–CH₃ | $n_D^{20}$: 1.5536 |
| 36 | 4-C₂H₅–C₆H₄–O–C₆H₄–O–CH₂–CH₂–C(CH₃)(CH₂CH₃)–OCH₃ | $n_D^{20}$: 1.5385 |
| 37 | 4-C₂H₅–C₆H₄–O–C₆H₄–O–CH₂–CH=C(CH₃)(Cl) | $n_D^{20}$: 1.5662 |
| 38 | C₆H₅–O–C₆H₄–O–CH₂–CH=C(CH₃)–CH₂–CH(CH₃)₂ | $n_D^{20}$: 1.5475 |
| 39 | C₆H₅–O–C₆H₄–O–CH(CH₃)–CH₂–CH(CH₃)₂ | $n_D^{20}$: 1.5335 |
| 40 | C₆H₅–O–C₆H₄–O–CH₂–CH₂–C(CH₃)₂–OCH₂CH₃ | $n_D^{20}$: 1.5369 |
| 41 | C₆H₅–O–C₆H₄–O–CH₂–CH₂–CH₂–C(CH₃)(CH₂CH₃)–OCH₃ | $n_D^{20}$: 1.5388 |
| 42 | C₆H₅–O–C₆H₄–O–CH(CH₃)–CH₂–CH₂–CH₂–C(CH₃)(CH₂CH₃)–OCH₃ | $n_D^{20}$: 1.5350 |
| 43 | C₆H₅–O–C₆H₄–CH(CH₃)–O–CH₂–CH=cyclohexyl(H) | $n_D^{20}$: 1.5602 |
| 44 | C₆H₅–O–C₆H₄–CH(CH₃)–O–CH₂–CH=C(CH₃)–CH₂–CH₃ | $n_D^{20}$: 1.5468 |
| 45 | C₆H₅–O–C₆H₄–O–CH₂–CH=C(CH₃)–CH=CH₂ | $n_D^{20}$: 1.5806 |
| 46 | C₆H₅–O–C₆H₄–O–CH₂–CH₂–CH₂–C≡CH | $n_D^{20}$: 1.5652 |
| 47 | C₆H₅–O–C₆H₄–O–CH₂–CH₂–C(CH₃)(CH₂CH₃)–O–CH₂–CH₃ | $n_D^{20}$: 1.5360 |

-continued

| Cpd. No. | Active substance | Physical data |
|---|---|---|
| 48 | 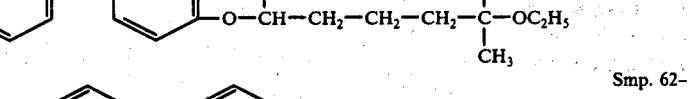 | $n_D^{20}$: 1,5260 |
| 49 | 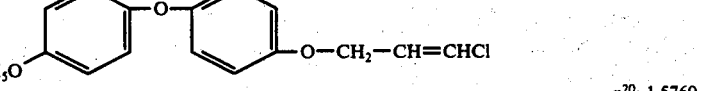 | Smp. 62–64° C |
| 50 | 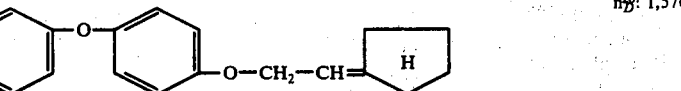 | $n_D^{20}$: 1,5760 |
| 51 |  | $n_D^{20}$: 1,5558 |
| 52 | 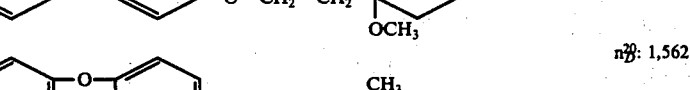 | $n_D^{20}$: 1,5628 |
| 53 | 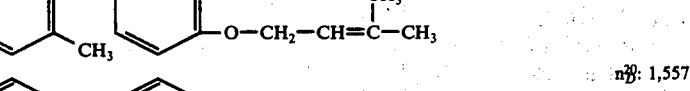 | $n_D^{20}$: 1,5572 |
| 54 | 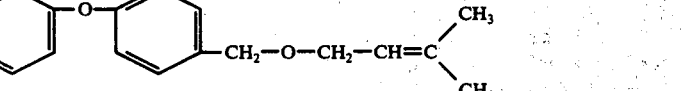 | $n_D^{20}$: 1,5774 |
| 55 | 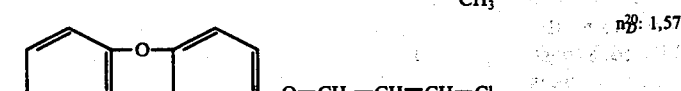 | |
| 56 | 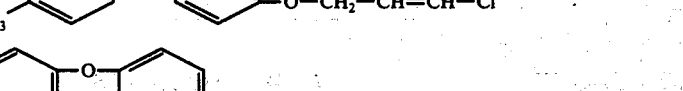 | |

EXAMPLE 7

Inhibitory Effect on Larvae of Dysdercus fasciatus

Ten larvae of Dysdercus fasciatus, which were 8–10 days before moulting into the adult stage, were topically treated with acetonic active-substance solutions. The larvae were then kept at 28° C with 80–90% relative humidity; they were fed on the shred of presoaked cottonseed. After ca. 10 days, i.e. as soon as the test insects had completed moulting, the insects were examined to determine the number of normal adults. The compounds according to Examples 1 to 6 including the compounds cited on pages 31 to 39 exhibited a high degree of effectiveness in the above test. Some values are indicated in the table below under "A".

EXAMPLE 8

Contact Action on Dysdercus fasciatus Larvae

A specific amount of a 0.1% solution of active substance in acetone (corresponding to 10 mg/of active substance/m²) was pipetted into an aluminium dish and evenly distributed.

After the acetone had evaporated, 10 larvae of the 5th. stage of Dysdercus fasciatus were put onto the treated dish which contained feed and moist cotton wool. The dish was then covered with a sieve cover. After about 10 days, i.e. as soon as the control larvae had shed and emerged to the adult stage, the test subjects were examined for the number of normal larvae.

The compounds according to Examples 1 to 6 including the compounds cited on pages 31 to 39 exhibited a high degree of effectiveness in the above test. Some values are indicated in the table below under "B".

EXAMPLE 9

Topical Action on Dermestes lardarius Pupae

10 Fresh pupae of Dermestes lardarius were treated topically with solutions of active substance in acetone. The pupae were then kept at 28° C and 80–90% relative humidity. After about 10 days, i.e. as soon as the controls had left their cocoons as Imagines, the test subjects were examined for the number of normal adults. The compounds according to Examples 1 to 6 including the compounds cited on pages 31 to 39 exhibited a high degree of effectiveness in the above test. Some values are indicated in the table below under "C".

EXAMPLE 10

Contact Action on *Tenebrio molitor* Pupae

A specific amount of a solution of active substance in acetone (corresponding to 1 mg of active substance/m²) was pipetted into an aluminium dish and evenly distributed.

After the acetone had evaporated, 10 freshly shed pupae were laid on the treated surface. The dish was covered with a sieve cover.

After the controls had left their coccons as Imagines the test subjects were examined for the number of normal adults. The compounds according to Examples 1 to 6 including the compounds cited on pages 31 to 39 exhibited a high degree of effectiveness in the above test. Some values are indicated in the table below under "D".

EXAMPLE 11

Contact Action on *Aedes aegypti* Larvae

About 20 2-day old larvae of the yellow fly (*Aedes aegypti*) were put into a beaker containing a solution of the active substance (concentration 10 ppm.) The beaker was then covered with a sieve cover. After the controls had shed and emerged to the adult stage, the test subjects were examined and the number of normal adults ascertained in comparison to the control. The compounds according to Examples 1 to 6 including the compounds cited on pages 31 to 39 exhibited a high degree of effectiveness in the above test. Some values are indicated in the table below under "E".

Table

| Compound No. | Percentage of normal adults in comparison to the untreated control | | | | |
|---|---|---|---|---|---|
| | A | B | C | D | E |
| 7 | 0 | — | — | — | — |
| 8 | 0 | — | 0 | — | — |
| 9 | — | — | 0 | — | — |

Table-continued

| Compound No. | Percentage of normal adults in comparison to the untreated control | | | | |
|---|---|---|---|---|---|
| | A | B | C | D | E |
| 10 | — | — | 0 | — | — |
| 6 | — | — | 0 | — | — |
| 36 | — | 0 | — | 0 | 0 |
| 11 | — | 0 | — | — | — |
| 13 | 0 | — | 0 | — | — |
| 14 | — | — | — | 0 | 0 |
| 15 | — | 0 | — | 0 | 0 |
| 17 | — | — | — | 0 | 0 |
| 19 | 0 | — | 0 | — | — |
| 18 | — | 0 | — | 0 | 0 |
| 20 | 0 | — | 0 | — | — |
| 21 | — | 0 | — | 0 | 0 |
| 22 | — | — | — | 0 | 0 |
| 23 | — | 0 | — | 0 | 0 |
| 24 | — | — | — | 0 | — |
| 25 | — | — | — | 0 | — |
| 26 | — | — | — | 0 | 0 |
| 27 | — | — | 0 | — | — |
| 33 | — | 0 | — | 0 | 0 |
| 2 | — | — | 0 | — | — |
| 28 | — | 0 | — | 0 | 0 |
| 42 | — | 0 | — | — | — |
| 45 | — | 0 | — | 0 | 0 |
| 46 | — | 0 | — | 0 | 0 |
| 31 | — | — | — | 0 | — |
| 33 | — | — | — | — | 0 |
| 34 | — | 0 | — | 0 | 0 |
| 38 | — | 0 | — | 0 | 0 |
| 39 | — | 0 | — | — | — |
| 40 | — | 0 | — | 0 | 0 |
| 41 | — | 0 | — | 0 | 0 |
| 42 | — | 0 | — | — | — |
| 43 | — | 0 | — | — | — |
| 47 | — | 0 | — | 0 | 0 |
| 50 | — | — | — | 0 | 0 |
| 51 | — | — | — | 0 | 0 |
| 53 | — | — | — | — | 0 |
| 49 | — | — | — | — | 0 |
| 55 | 0 | — | 0 | — | — |
| 56 | 0 | — | 0 | — | — |
| 48 | — | — | 0 | — | — |

COMPARISON TEST

The following known compounds having a similar structure, have been tested by the same methods as indicated above. The results show a rather inferior activity.

| Compound | Percentage of normal adults in comparison to the untreated control | | | | |
|---|---|---|---|---|---|
| | A | B | C | D | E |
| 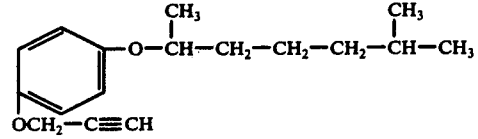 | 100 | — | 100 | — | — |
| 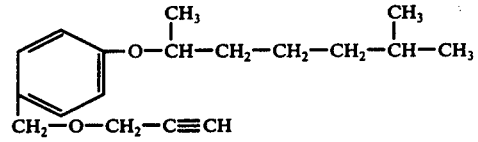 | 100 | — | 100 | — | — |
| 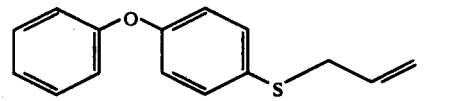 U.S. Pat. No. 3 155 733 | — | 100 | — | 0 | 100 |

| Compound | Percentage of normal adults in comparison to the untreated control | | | | |
|---|---|---|---|---|---|
|  | A | B | C | D | E |
| 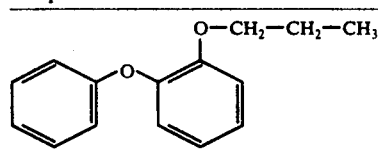 C.A. Vol. 30 (1936)8186 | — | 100 | — | 100 | — |
| 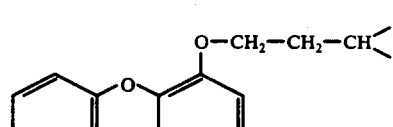 C.A. Vol. 30 (1936)8186 | — | 100 | — | 100 | — |

I claim:
1. 1-Phenoxy-4-(3-methyl-3-methoxy-pentyl-1-oxy)-benzene.
2. 1-Phenoxy-4-(3-chloro-2-butenyl-1-oxy)-benzene.
3. 1-Phenoxy-4-(3-methyl-2-penten-4-inyl-1-oxy)-benzene.
4. 1-Phenoxy-4-(3,3-dichloro-2-propenyl-1-oxy)-benzene.
5. 1-Phenoxy-4-(3-chloro-2-propenyl-1-oxy)-benzene.
6. 1-Phenoxy-4-(3-methoxy-butyl-1-oxy)-benzene.
7. 1-Phenoxy-4-(3,5-dimethyl-2-hexenyl-1-oxy)-benzene.
8. 1-Phenoxy-4-(3-methyl-3-ethoxy-butyl-1-oxy)-benzene.
9. 1-Phenoxy-4-(4-pentinyl-1-oxy)-benzene.

* * * * *